United States Patent
Poigny et al.

(10) Patent No.: US 8,961,944 B2
(45) Date of Patent: Feb. 24, 2015

(54) USE OF DELTA-TOCOPHERYL-CARBOHYDRATE AS A DEPIGMENTING AGENT

(75) Inventors: Stéphane Poigny, Saubens (FR); Françoise Belaubre, Villeneuve Tolosane (FR); Jean-Hilaire Saurat, Geneve Suisse (FR); Olivier Sorg, Geneve Suisse (FR); Behrooz Kasraee, Geneve Suisse (FR)

(73) Assignee: Pierre Fabre Dermo-Cosmetique, Boulogne-Billancourt (FR)

( * ) Notice: Subject to any disclaimer, the term of this patent is extended or adjusted under 35 U.S.C. 154(b) by 12 days.

(21) Appl. No.: 13/319,712

(22) PCT Filed: May 12, 2010

(86) PCT No.: PCT/EP2010/056533
§ 371 (c)(1),
(2), (4) Date: Dec. 6, 2011

(87) PCT Pub. No.: WO2010/130776
PCT Pub. Date: Nov. 18, 2010

(65) Prior Publication Data
US 2012/0093749 A1    Apr. 19, 2012

(30) Foreign Application Priority Data
May 14, 2009 (FR) ................... 09 53180

(51) Int. Cl.
*A61K 8/00* (2006.01)
*A61K 8/02* (2006.01)
*A61K 8/67* (2006.01)
*A61K 8/34* (2006.01)
*A61K 8/36* (2006.01)
*A61K 8/49* (2006.01)
*A61K 8/92* (2006.01)
*A61Q 19/02* (2006.01)

(52) U.S. Cl.
CPC ............ *A61K 8/678* (2013.01); *A61K 8/347* (2013.01); *A61K 8/361* (2013.01); *A61K 8/498* (2013.01); *A61K 8/671* (2013.01); *A61K 8/922* (2013.01); *A61Q 19/02* (2013.01); *A61K 2800/57* (2013.01)
USPC ........................................... 424/62; 424/401

(58) Field of Classification Search
None
See application file for complete search history.

(56) References Cited

U.S. PATENT DOCUMENTS

| 4,617,292 A | 10/1986 | Satoh et al. |
| 6,569,906 B1 | 5/2003 | Redoules et al. |
| 2006/0018867 A1* | 1/2006 | Kawasaki et al. ........ 424/70.122 |
| 2010/0168045 A1 | 7/2010 | Bordat et al. |

FOREIGN PATENT DOCUMENTS

| FR | 2775976 A1 | 9/1999 |
| FR | 2894577 A1 | 6/2007 |
| WO | WO 2007/091694 A1 | 8/2007 |

OTHER PUBLICATIONS

International Search Report issued in PCT/EP2010/056533, dated Jul. 25, 2011.

* cited by examiner

*Primary Examiner* — Dennis J Parad
(74) *Attorney, Agent, or Firm* — Birch, Stewart, Kolasch & Birch, LLP

(57) ABSTRACT

The present invention relates to a cosmetic or pharmaceutical composition for cutaneous application, whose goal is the depigmentation of the skin.

3 Claims, No Drawings

USE OF DELTA-TOCOPHERYL-CARBOHYDRATE AS A DEPIGMENTING AGENT

The present invention relates to cosmetic and dermatological preparations containing delta-tocopheryl-carbohydrate for the treatment of cosmetic or dermatological changes of the skin relating to hyperpigmentation, in a localised manner, such as for example beauty spots or freckles, or in a more generalised manner, such as for large areas of skin. The hyperpigmentation can be natural or induced by the environment.

Melanocytes, which are star-shaped cells, are responsible for skin pigmentation and are found in the deepest layer of the epidermis, i.e. the basal layer. The principal function of melanocytes is to ensure melanogenesis, the process by which melanin is synthesised in specialised organelles called melanosomes. Melanosomes, containing melanin, are then transported and distributed to nearby keratinocytes via the dendrites of the melanocytes. This contact with the keratinocytes results in cutaneous pigmentation, a mechanism that protects the skin against the mutagenic effects of ultraviolet rays. Several physiological stimuli can be responsible for the synthesis of melanin.

A natural and normal physiological stimulus of the synthesis of melanin is the sun, which causes an increase in the number of melanocytes, neosynthesis of melanin, and morphological changes of melanocytes, combining an increase in their dendricity with an increase in the transfer of melanosomes to the keratinocytes.

At the molecular level, melanogenesis consists of a series of enzymatic reactions whose precursor is tyrosine. In the case of exposure to the sun, this exposure stimulates the synthesis and secretion of alpha-melanocyte-stimulating hormone (α-MSH). α-MSH increases the intra-melanocyte concentration of cyclic AMP, activating a transcription factor, microphthalmia-associated transcription factor" (Mitf), which in turn stimulates the transcriptional activity of genes coding for three enzymes that principally participate in the process of melanogenesis: tyrosinase and tyrosinase-related proteins 1 and 2 (TRP-1 and TRP-2).

Tyrosinase and TRP-1 and TRP-2 are also active and responsible for pigmentation when the stimulus is other than the sun.

Tyrosinase catalyses the transformation of tyrosine into dopaquinone. From that point, two synthetic pathways are possible: eumelanogenesis and pheomelanogenesis. Dopaquinone is converted into eumelanin by a successive series of oxidation reactions utilising TRP-1 and TRP-2. Eumelanin corresponds to black and brown pigments, with low sulphur content, and ensures photoprotector capacity. In pheomelanogenesis, molecules with high sulphur content are incorporated in dopaquinone to give pheomelanin, of orange-yellow colour, which is present in the skin of red-haired subjects.

Melanogenesis can be inhibited by the interruption of enzymatic oxidation reactions that use tyrosinase and/or TRP-1 and/or TRP-2. Melanogenesis can also be inhibited by the interruption of dopaquinone polymerization.

Interruption of melanogenesis can thus have several causes. Certain exogenous molecules are known to negatively regulate melanogenesis. Hydroquinone inhibits the synthesis of melanin by presenting itself in the form of a tyrosinase substrate in order to divert its activity. Arbutin containing hydroquinone acts in the same manner. Kojic acid decreases the activity of tyrosinase but also acts as a powerful reducer by preventing the colouring of melanin by oxidation. Vitamin A decreases the expression of TRP-2 tyrosinase.

In particular, the family of tocopherols contains depigmenting agents known in the literature. Alpha-tocopherol, or vitamin E, is found naturally in many plants, usually with other compounds such as beta-tocopherol, gamma-tocopherol or delta-tocopherol. Cosmetic depigmenting compositions containing these tocopherols are already on the market.

However, it was shown that under mild oxidation conditions, the direct application of these antioxidants on the skin causes pro-inflammatory effects which are the consequence of hyperactivity at the concentrations typically used. Thus, several structural modifications of these tocopherols have made it possible to limit side effects, enabling their use in the treatment or prevention of other skin diseases or problems.

Thus, WO 98/51679 describes tocopherol esters in cosmetic or pharmaceutical compositions. This international request disclosed that these tocopherol esters have anti-radical and anti-inflammatory activities, support differentiation of keratinocytes, improve cutaneous hydration and smoothness of the skin, and have anti-ageing or depigmenting activity.

Better, EP 1,062,223 described precursors of active compounds used in cosmetology or dermatology, more particularly in the treatment of skin diseases (atopic dermatitis, acne, psoriasis). The principle of the invention is related to the use of glucocerebrosidase, which is a lysosomal enzyme present in all cells and thus naturally present in the skin. Glucocerebrosidase hydrolyses the precursor of the active compound, thus releasing the biologically active substance. By this means, side effects are decreased, even eliminated. EP 1,062,223 thus discloses the use of carbohydrate precursors of delta-tocopherol. EP 1,062,223 more particularly discloses the physicochemical and biological characteristics of delta-tocopheryl-glucopyranoside. The enzymatic hydrolysis by glucocerebrosidase of delta-tocopheryl-glucopyranoside slowly releases delta-tocopherol, with lower kinetics than a reference derivative (4-methylumbelliferyl glucopyranoside). This slow release avoids the over-concentration of the active substance delta-tocopherol and thus any inflammatory effect during application of the product. Thus, the slow release of the active substance ensures its better bioavailability in the cutaneous medium and thus more effective protection.

The very low activity of glucoconjugates compared with that of the free active substance is in particular disclosed in EP 1,062,223: in particular, delta-tocopheryl-glucopyranoside has weak antioxidant capacity compared to that of delta-tocopherol. Thus, and according to the above-mentioned mechanistic knowledge, the depigmenting activity of delta-tocopheryl-glucopyranoside should be equal or less in comparison with that of delta-tocopherol.

However to date, it has been noted in a very surprising way that in an inverse manner delta-tocopheryl-glucopyranoside has a depigmenting activity quite higher than that of delta-tocopherol which it releases during application on the skin (see example 1). This effect cannot be explained by the sole release of delta-tocopherol and is completely unexpected.

The object of the invention consequently relates to the use of a delta-tocopheryl-carbohydrate of Formula I:

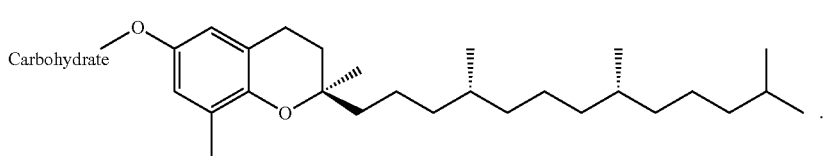

Formula I as a cosmetic depigmenting agent.

A delta-tocopheryl-carbohydrate consists of two fragments bound to one another. One fragment is the carbohydrate and the other is the delta-tocopherol. The terms monosaccharide, saccharide, carbohydrate and sugar are equivalent in the present invention.

The carbohydrate can be bound to the delta-tocopherol by α or β glycosidic bonds if the bond is on the anomeric carbon of the carbohydrate. The carbohydrate can also be bound to the delta-tocopherol by a simple ether bond if the bond is made on the oxygen of a non-anomeric carbon of the carbohydrate.

Advantageously, the carbohydrate of Formula I is selected among the monosaccharides.

More advantageously, the carbohydrate of Formula I is selected among the series D monosaccharides.

Still more advantageously, the carbohydrate of Formula I is selected among the $C_3$-$C_6$ series D monosaccharides such as glyceraldehyde, erythrose, threose, ribose, arabinose, xylose, lyxose, alose, altrose, gulose, idose, talose, glucose, galactose, mannose and fructose as well as the derivatives of same like their cyclic forms when they exist, such as pyrannose or furanose for example. The preferred monosaccharide in the present invention is D-glucopyrannose.

The delta-tocopheryl-carbohydrate used according to the invention is the delta-tocopheryl-glucopyranoside defined by the following Formula II:

dermo-cosmetically acceptable vehicle and an effective quantity of delta-tocopheryl-carbohydrate of Formula I, preferably of Formula II.

"Vehicle" means any adjuvant or excipient enabling the manufacture, preservation, or administration of the pharmaceutical composition. Any acceptable vehicle from the dermo-cosmetic point of view, selected for example among the excipients typically used in pharmaceutical formulations, can be used in the composition according to the invention. Advantageously, the inventive compound contains from 0.01% to 5% by weight of delta-tocopheryl-carbohydrate of Formula I, preferably 0.03% to 2.5% by weight of delta-tocopheryl-carbohydrate of Formula I, more preferably between 0.05% and 1% by weight of delta-tocopheryl-carbohydrate of Formula I compared to the total weight of the composition.

Preferably, the inventive compound contains from 0.01% to 5% by weight of delta-tocopheryl-glucopyranoside of Formula II, preferably 0.03% to 2.5% by weight of delta-tocopheryl-glucopyranoside of Formula II, more preferably between 0.05% and 1% by weight of delta-tocopheryl-glucopyranoside of Formula II compared to the total weight of the composition.

The inventive compound can be provided in the form of an oil-in-water (O/W) or water-in-oil (W/O) emulsion. It can be further provided in the form of spherules such as liposomes, nanocapsules or nanospheres.

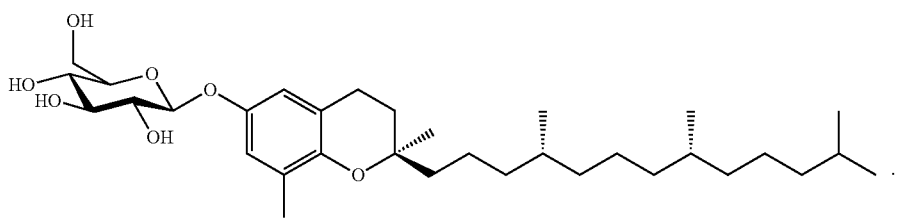

Formula II

In the present invention, delta-tocopheryl-carbohydrate is used as a cosmetic depigmenting agent. The depigmenting function of delta-tocopheryl-carbohydrate can be supplemented by any additional physiological effect resulting from its mode of action.

The precursors of the active substance or conjugated compounds according to the invention can be obtained by a biochemical process or by organic synthesis. According to an organic synthesis process, the active substance is coupled with the carbohydrate, previously tetra-acylated and activated in position 1 (epimeric carbon, also called anomeric carbon) by an imidate. The acetyl groups are then hydrolyzed by methanolate ions. Other synthesis techniques, well known to the person skilled in the art, can be used in order to synthesise these molecules or analogue molecules with an ether function on another carbon position (2, 3, 4, 5, or 6), for example.

Another object of the invention relates to a cosmetic depigmenting composition comprising as active ingredient a The oil phases that can be used in the invention are:
solid or thick oil phases such as beeswaxes, candelilla waxes, carnauba wax, petroleum wax (or microcrystalline waxes), paraffin; and mixtures of same;
oils of animal and/or plant origins; and mixtures of same;
hydrocarbon oils of synthetic origin, with more than 8 carbon atoms, either linear or branched, saturated or unsaturated, such as hydrogenated polyisobutylene (Parleam oil), paraffin oil (or Vaseline, or mineral oil), isoparaffins, limonene, squalene, polyisobutene or isooctane; and mixtures of same;
oils formed of higher fatty acids, in particular $C_{10}$-$C_{22}$, such as myristic acid, palmitic acid, stearic acid, behenic acid, oleic acid, linoleic acid, linolenic acid or isostearic acid;
oils formed of higher fatty alcohol, in particular $C_{10}$-$C_{22}$, such as oleic alcohol, linoleic or linolenic alcohol, isostearic alcohol or octyl dodecanol; and mixtures of same;

oils formed of linear or branched, saturated or unsaturated esters of Formula RCOOR', wherein R represents the remainder of a higher fatty acid comprising from 7 to 19 carbon atoms and R' represents a hydrocarbon chain comprising from 3 to 20 carbon atoms, in particular $C_{12}$-$C_{36}$ esters such as isopropyl myristate, isopropyl palmitate, butyl stearate, hexyl laurate, diisopropyle adipate, isononyl isononanoate, 2-ethyl-hexyl palmitate, 2-hexyl-decyle laurate, 2-octyldecyle palmitate, 2-octyl-dodecyle myristate or lactate, di(2-ethyl-hexyl) succinate, diisostearyl malate, isostearyl hydroxystearate, ethylhexyl hydroxystearate, cetearyl ethylhexanoate; isostearyl isostearate; and mixtures of same;

oils formed of $C_1$-$C_{30}$ carboxylic acid monoglycerides, $C_1$-$C_{30}$ carboxylic acid diglycerides, $C_1$-$C_{30}$ carboxylic acid triglycerides, such as caprylic and capric acid mono-, di- or triglycerides, palmitic acid mono-, di- and triglycerides, linoleic acid mono-, di- and triglycerides, stearic acid mono-, di- and triglycerides, isostearic acid mono-, di- and triglycerides, behenic acid mono-, di- and triglycerides, oleic acid mono-, di- and triglycerides, myristic acid mono-, di- and triglycerides, linolenic acid mono-, di- and triglycerides; and mixtures of same;

non-volatile siliconated oils such as non-volatile polydimethylsiloxanes (PDMS); modified polysiloxanes; aminated silicones, or silicones with hydroxyl groups, or fluorinated; dimethicones; trimethicones; and mixtures of same. Preferably, the dimethicones that can be used in the context of the present invention are available under the brand names VICASIL® (General Electric Company), DOW CORNING 200® (Dow Corning Corporation, DC200), DOW CORNING 225®, or any other oil phase known to the person skilled in the art.

The composition can also comprise agents for conditioning the skin.

Examples of agents for conditioning the skin include, but are not limited to, anionic, cationic or non-ionic emulsifiers such as sodium lauryl sulphate, sodium dioctyl sulfosuccinate, sodium stearate, sorbitan ester, ethoxyl fatty acids, ethoxyl fatty alcohols, trideceth-9 and PEG-5 ethylhexanoate, and any emulsifier and conditioning agent known to the person skilled in the art; and mixtures of same.

For the inventive compositions having an alcoholic-aqueous or alcoholic base, the use of any mono-alcohol is suitable.

The composition can further include a polyol that is miscible with water at room temperature (25° C.) notably chosen among polyols having in particular from to 20 carbon atoms, preferably having from 2 to 10 carbon atoms, and preferentially having from 2 to 6 carbon atoms, such as glycerin, glycol derivatives such as propylene glycol, butylene glycol, pentylene glycol, hexylene glycol, dipropylene glycol, diethylene glycol; glycol ethers such as mono-, di- or tripropylene glycol alkyl($C_1$-$C_4$) ethers, mono-, di- or triethylene glycol alkyl($C_1$-$C_4$) ethers; and mixtures of same.

The composition can further include antioxidant agents chosen among the amino acids (for example glycine, histidine, tyrosine, tryptophan) and derivatives of same, imidazols and derivatives of same, peptides such as D,L-carnosine, D-carnosine, L-carnosine and derivatives of same, caratenoids, carotenes and derivatives of same, chlorogenic acids and derivatives of same, lipoic acids and derivatives of same (for example dihydrolipoic acid), thiols (for example thioredoxine, glutathione, cysteine, cystine, cystamine and glycosyl, N-acetyl, methyl, ethyl, propyl, amyl, butyl and lauryl, palmitoyl, oleyl, cholesteryl and glyceryl ester, aurothioglucose, propylthiouracil and derivatives of same), sulfoximine compounds (for example buthionine sulfoximine, homocysteine and derivatives of same) in low-tolerance doses (i.e. pmol/kg), and also chelating agents (hydroxylated fatty acids, phytic acid, lactoferrin, citric acids, lactic acid, maleic acid, EDTA, disodium EDTA, EGTA and derivatives of same), unsaturated fatty acids and derivatives of same, folic acid and derivatives of same, ubiquinone and ubiquinol and derivatives of same, vitamin C and derivatives of same (for example ascorbyl palmitate), vitamin A and derivatives of same, rutinic acid, carnosine, uric acid, mannose and derivatives of same, zinc and derivatives of same (for example ZnO, $ZnSO_4$), selenium and derivatives of same (for example selenomethionine), stilbenes and derivatives of same (for example oxidized stilbene), superoxide dismutase and its derivatives, and other antioxidants well known to the person skilled in the art; and mixtures of same.

The composition can further include antimicrobial agents such as preservatives or antifungals chosen among alcohols, which may contain one or more aromatic substituents, for example phenoxyethanols such as 2-phenoxyethanol, 1-phenoxy-2-propanol, benzylic alcohol, 2-hydroxybiphenyl, parabens, preferentially methylparaben, ethylparaben, propylparaben, butylparaben, isobutylparaben, sodium methylparaben, sodium ethylparaben, sodium propylparaben, sodium isobutylparaben, sodium butylparaben or sodium isobutylparaben, imidazolidinyl urea, diazolidinyl urea, sodium hydroxymethylglycinate, halogenous derivatives such as iodopropynyl butylcarbamate, 2-bromo-2-nitropropan-1,3-diol, 2,4,4'-trichloro-2'-hydroxydiphenylether (triclosan), 3,4,4'-trichlorocarbanilide (triclocarban), chlorbutanulum, 2,4-dichlorobenzylic alcohol, urea of N-(4-chlorophenyl-N'-(3,4-dichlorphenyl), 1,2-dibromo-2,4-dicyanobutane, chloroxylenol, ketoconazole, oxiconazole, butoconazole, clotrimazole, econazole, enilconazole, fenticonazole, miconazole, sulconazole, tioconazole, fluconazole, itraconazole, terconazole, active substances containing one or more cationic nitrogens such as cetyltrimethylammonium chloride, cetylpyridinium chloride, benzethonium chloride, diisobutylethoxyethyl-dimethylbenzylammonium chloride, diisobutyl-phenoxy-ethoxyethyl-dimethylbenzyl-ammonium chloride, chloride, bromide, N-alkyl-N,N-dimethylbenzyl-ammonium saccharinate, trimethylammonium chloride, sodium aluminium chlorohydroxylacetate, tricetylmethylammonium chloride, diaminoalkylamide, organic acids and their salts, such as citric acid, unsaturated antimicrobial agents such as farnesol, terbinafine or naftifine, heterocyclic aromatic agents such as bifonazole, cloconazole, isoconazole, or any other antimicrobial antifungal agent known to the person skilled in the art; and mixtures of same.

The composition can further include thickening agents or agents that modify rheology, such as for example hydrophobically modified ethoxylated non-ionic urethanes, polycarboxylic acid thickeners such as acrylates/steareth-20 methacrylate copolymer, carbomers, acrylate copolymers and cross-linked $C_{10}$-$C_{30}$ alkyl acrylates; and mixtures of same.

The composition can further include acids and bases to adjust the pH range of the aforesaid composition. The bases can be mineral (soda, potash, ammonia) or organic such as mono-, di- or triethanolamine, an aminomethylpropanediol, N-methyl-glucamine, basic amino acids such as arginine and lysine; and mixtures of same.

The compositions can further include one or more additional ingredients such as pH buffers, vitamins, fragrances, and any other useful compound known to the person skilled in the art.

The cosmetic composition of the invention can be conditioned in the form of a pomade, a spray, a lotion, a gel, a foam, a dispersion, a serum, a mask, a body milk or a cream, for example.

In order to strengthen the depigmenting activity of the delta-tocopheryl-carbohydrate of Formula I or II, it can be combined with at least one other depigmenting agent. The depigmenting agent combined with the delta-tocopheryl-carbohydrate of Formula I or II in the depigmenting composition is selected among hydroxylated diphenylmethane derivatives, in particular 4-(1-phenylethyl)-1,3-dihydroxybenzene, retinoids, in particular retinal, 4-butyl-resorcinol (which is sold under the brand name Rucinol®), kojic acid, linoleic acid and an oil rich in linoleic acid in triglycerate form, in particular evening primrose oil, or mixtures of same.

Advantageously, the depigmenting agent combined with the delta-tocopheryl-carbohydrate of Formula I or II in the depigmenting composition is 4-(1-phenylethyl)-1,3-dihydroxybenzene. Thus, the inventive compositions contain from 0.01% to 10%, preferably 0.1% to 5%, of 4-(1-phenylethyl)-1,3-dihydroxybenzene compared to the total weight of the composition.

Advantageously, the depigmenting agent combined with the delta-tocopheryl-carbohydrate of Formula I or II in the depigmenting composition, is retinal. Thus, the inventive compositions contain from 0.001% to 5%, and preferably 0.01% to 1%, of retinal compared to the total weight of the composition.

Advantageously, the depigmenting agent combined with the delta-tocopheryl-carbohydrate of Formula I or II in the depigmenting composition is linoleic acid. Thus, the inventive compositions contain from 0.01% to 5%, preferably 0.1% to 5%, of linoleic acid compared to the total weight of the composition.

Advantageously, the depigmenting agent combined with the delta-tocopheryl-carbohydrate of Formula I or II in the depigmenting composition is a plant oil rich in linoleic acid in the form of triglycerate. Thus, the inventive compositions contain from 0.01% to 5%, preferably 0.1% to 5%, of a plant oil rich in linoleic acid in the form of triglycerate compared to the total weight of the composition. An example of a plant oil rich in linoleic acid in the form of triglycerate is evening primrose oil.

Advantageously, the depigmenting agent combined with the delta-tocopheryl-carbohydrate of Formula I or II in the depigmenting composition is evening primrose oil. Thus, the inventive compositions contain from 0.01% to 5%, and preferably 0.1% to 5%, of evening primrose oil compared to the total weight of the composition.

Advantageously, the depigmenting agent combined with the delta-tocopheryl-carbohydrate of Formula I or II in the depigmenting composition is 4-butyl-resorcinol. Thus, the inventive compositions contain from 0.01% to 5%, preferably 0.1% to 1%, of 4-butyl-resorcinol compared to the total weight of the composition.

Advantageously, the depigmenting agent combined with the delta-tocopheryl-carbohydrate of Formula I or II is kojic acid. Thus, the inventive compositions contain from 0.01% to 10%, preferably 0.1% to 5%, of kojic acid compared to the total weight of the composition.

Advantageously, the inventive depigmenting compound contains as depigmenting active ingredient a mixture of delta-tocopheryl-carbohydrate of Formula I or II, 4-(1-phenylethyl)-1,3-dihydroxybenzene, retinal and a plant oil rich in linoleic acid in triglycerate form. In particular, the plant oil rich in linoleic acid in triglycerate form used in this mixture is evening primrose oil.

Advantageously, the inventive depigmenting compound contains as depigmenting active ingredient a mixture of delta-tocopheryl-carbohydrate of Formula I or II, 4-(1-phenylethyl)-1,3-dihydroxybenzene, retinal and evening primrose oil.

Advantageously, another inventive depigmenting compound contains as depigmenting active ingredient a mixture of delta-tocopheryl-carbohydrate of Formula I or II, 4-(1-phenylethyl)-1,3-dihydroxybenzene, retinal and linoleic acid.

The present invention will be illustrated in a non-restrictive way by the following examples.

EXAMPLE 1

Comparison of Depigmenting Properties of Delta-Tocopheryl-Glucopyranoside, Delta-Tocopherol and Alpha-Tocopherol B16-F10 cells are inoculated in 96-well plates in DMEM (Dulbecco's Modified Eagle's Medium) supplemented with Foetal Calf Serum (FCS) and incubated for 24 hours at 37° C., 5% $CO_2$. Melanogenesis is stimulated by α-MSH (0.1 μM) for 3 or 5 days. Each concentration of active substance is tested in triplicate. Total melanin and intracellular melanin dissolved in lysis buffer are then assayed by reading absorbance at 405 nm. Total proteins are assayed in the lysate according to protocol "SRD/TO/154/012" and the results are expressed in mg melanin/mg proteins. The percentage of activity is calculated as follows:

% inhibition=[(NMC+NMT)/NMC]×100

NMC being the normalised mean of the control
NMT being the normalised mean of the treated

TABLE 1

Measure of percent inhibition of intracellular melanin

| | Delta-tocopheryl-glucopyranoside | | Delta-tocopherol | | Alpha-tocopherol | |
|---|---|---|---|---|---|---|
| | 3 days | 5 days | 3 days | 5 days | 3 days | 5 days |
| 10 μM | 22% | 38% | Not active | Not active | Not active | Not active |
| 50 μM | 68% | 90% | 41% | 48% | Not active | Not active |

EXAMPLE 2

Example of Composition

TABLE 2 formulation of a cream gel according to the present invention.

| Ingredients (brand names) | INCI designation | Percentage by weight | Function |
|---|---|---|---|
| I. Purified water | Water | QSP* 100% | |
| Hydrolite 5 ® | Pentylene glycol | 3 | Moistener, Preservative |
| EDTA, 2Na | Disodium EDTA | 0.1 | Sequestering agent |

TABLE 2-continued formulation of a cream gel according to the present invention.

| Ingredients (brand names) | INCI designation | Percentage by weight | Function |
|---|---|---|---|
| Microcare PM4 ® | Phenoxyethanol-parabens | 0.8 | Preservatives |
| Water-soluble PCL | Trideceth-9 & PEG-5 Ethylhexanoate | 1.5 | Aqueous emollient |
| II. Pemulen ® TR-1 | $C_{10}$-$C_{30}$ acrylate crosslinked alkyl acrylate copolymers | 0.5 | Gelling agent, stabilising agent |
| III. Stearin TP | Stearic acid | 2 | Emulsifier, consistency factor |
| Liquid PCL | Cetearyl ethylhexanoate & isopropyl myristate | 3 | Emollient |
| DC200 ® | Dimethicone | 0.3 | Emollient |
| Myritol ® 318 | Caprylic/capric triglycerides | 3 | Emollient |
| Primol ® 352 | Liquid paraffin | 2 | Emollient |
| IV. Active substance | 1. Delta-tocopheryl-glucopyranoside | 0.5 | Active substance |
| V. Soda | Soda | 0.08 | pH adjuster |

*QSP: "as much as suffices for"

EXAMPLE 3

Example of Composition

TABLE 3

Depigmenting composition comprising a mixture of depigmenting active ingredient.

| Ingredients (brand names) | INCI designation | Percentage by weight | Function |
|---|---|---|---|
| I. Purified water | Water | QSP* 100% | |
| Hydrolite 5 ® | Pentylene glycol | 3 | Moistener, Preservative |
| EDTA, 2Na | Disodium EDTA | 0.1 | Sequestering agent |
| Microcare PM4 ® | Phenoxyethanol-parabens | 0.8 | Preservatives |
| Water-soluble PCL | Trideceth-9 & PEG-5 Ethylhexanoate | 1.5 | Aqueous emollient |
| II. Pemulen ® TR-1 | $C_{10}$-$C_{30}$ acrylate crosslinked alkyl acrylate copolymers | 0.5 | Gelling agent, stabilising agent |

TABLE 3-continued

Depigmenting composition comprising a mixture of depigmenting active ingredient.

| Ingredients (brand names) | INCI designation | Percentage by weight | Function |
|---|---|---|---|
| III. Stearin TP | Stearic acid | 2 | Emulsifier, consistency factor |
| Liquid PCL | Cetearyl ethylhexanoate & isopropyl myristate | 3 | Emollient |
| DC200 ® | Dimethicone | 0.3 | Emollient |
| Myritol ® 318 | Caprylic/capric triglycerides | 3 | Emollient |
| Primol ® 352 | Liquid paraffin | 2 | Emollient |
| IV. Active substances | 1. Delta-tocopheryl-glucopyranoside | 0.1 | Active substance |
| | 2. 4-(1-phenylethyl)-1,3-dihydroxybenzene | 0.5 | |
| | 3. Retinaldehyde | 0.05 | |
| | 4. Evening primrose oil | 1 | |
| V. Soda | Soda | 0.08 | pH adjuster |

*QSP: "as much as suffices for"

The invention claimed is:

1. A cosmetic depigmenting composition characterised in that it contains, in a dermo-cosmetically acceptable vehicle, from 0.03% to 2.5% by weight of the delta-tocopheryl-carbohydrate of Formula I

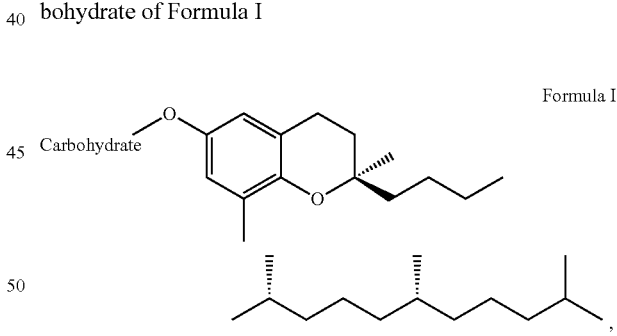

Formula I wherein "Carbohydrate" represents D-glucopyranoside, the percentages being expressed compared to the total weight of the aforesaid composition, said composition further comprising retinal and 4-(1-phenylethyl)-1,3-dihydroxybenzene.

2. The depigmenting cosmetic composition according to claim 1, characterised in that it contains as active depigmenting ingredient a mixture of 4-(1-phenylethyl)-1,3-dihydroxybenzene, said delta-tocopheryl-carbohydrate, retinal and evening primrose oil.

3. The cosmetic depigmenting composition of claim 1, containing from 0.05% to 1% by weight of the delta-tocopheryl-carbohydrate of Formula II Formula II
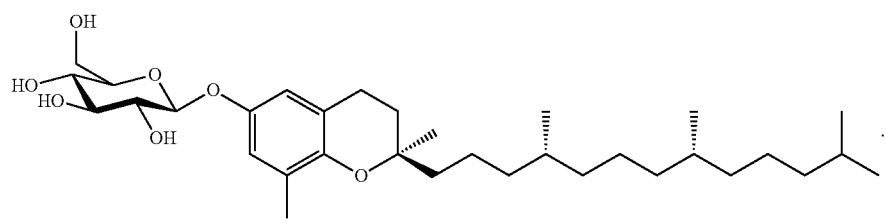
* * * * *